United States Patent
Howard et al.

(10) Patent No.: US 12,430,019 B2
(45) Date of Patent: Sep. 30, 2025

(54) SYSTEMS AND METHODS INCORPORATING A LIGHT THERAPY USER INTERFACE FOR OPTICAL MODULATION

(71) Applicant: Boston Scientific Neuromodulation Corporation, Valencia, CA (US)

(72) Inventors: Joshua Dale Howard, Sacramento, CA (US); Michael A. Moffitt, Solon, OH (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 175 days.

(21) Appl. No.: 18/397,740

(22) Filed: Dec. 27, 2023

(65) Prior Publication Data
US 2024/0220094 A1    Jul. 4, 2024

Related U.S. Application Data

(60) Provisional application No. 63/437,050, filed on Jan. 4, 2023.

(51) Int. Cl.
G06F 3/048     (2013.01)
G06F 3/04847   (2022.01)
A61N 5/06      (2006.01)

(52) U.S. Cl.
CPC ........ *G06F 3/04847* (2013.01); *A61N 5/0601* (2013.01)

(58) Field of Classification Search
None
See application file for complete search history.

(56) References Cited

U.S. PATENT DOCUMENTS

| | | | |
|---|---|---|---|
| 4,920,979 A | 5/1990 | Bullara | |
| 5,076,270 A | 12/1991 | Stutz, Jr. | |

(Continued)

FOREIGN PATENT DOCUMENTS

| | | |
|---|---|---|
| EP | 2143373 A1 | 1/2010 |
| EP | 3020450 A1 | 5/2016 |

(Continued)

OTHER PUBLICATIONS

Extended European Search Report for European Patent Application No. 23209013.4 mailed Jul. 26, 2024.

(Continued)

*Primary Examiner* — Tuan S Nguyen
(74) *Attorney, Agent, or Firm* — Branch Partners PLLC; Bruce E. Black

(57) ABSTRACT

An optical modulation system includes a user interface including a plurality of user-selectable controls to select or adjust values for each of a plurality of modulation parameters and estimating a modulation dosage or irradiance at a target based on, at least, the target, a location of an optical modulation lead, values of the modulation parameters, and estimated light attenuation by tissue between the optical modulation lead and the target. An optical modulation system can limit selection of the value of at least one of the modulation parameters by at least one of a) an estimation of a modulation dosage at the target or b) an estimation of a dosage, temperature change, temperature, heating, or delivering energy at non-target issue.

19 Claims, 8 Drawing Sheets

(56) References Cited

U.S. PATENT DOCUMENTS

| | | |
|---|---|---|
| 5,437,193 A | 8/1995 | Schleitweiler et al. |
| 5,445,608 A | 8/1995 | Chen et al. |
| 5,556,421 A | 9/1996 | Prutchi et al. |
| 5,824,027 A | 10/1998 | Hoffer et al. |
| 6,175,710 B1 | 1/2001 | Kamaji et al. |
| 6,181,969 B1 | 1/2001 | Gord |
| 6,224,450 B1 | 5/2001 | Norton |
| 6,271,094 B1 | 8/2001 | Boyd et al. |
| 6,295,944 B1 | 10/2001 | Lovett |
| 6,364,278 B1 | 4/2002 | Lin et al. |
| 6,366,719 B1 | 4/2002 | Heath et al. |
| 6,391,985 B1 | 5/2002 | Goode et al. |
| 6,442,435 B2 | 8/2002 | King et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 6,988,001 B2 | 1/2006 | Greatbatch et al. |
| 6,993,384 B2 | 1/2006 | Bradley et al. |
| 7,190,993 B2 | 3/2007 | Sharma et al. |
| 7,203,548 B2 | 4/2007 | Whitehurst et al. |
| 7,244,150 B1 | 7/2007 | Brase et al. |
| 7,252,677 B2 | 8/2007 | Burwell et al. |
| 7,288,108 B2 | 10/2007 | DiMauro et al. |
| 7,395,118 B2 | 7/2008 | Erickson |
| 7,437,193 B2 | 10/2008 | Parramon et al. |
| 7,450,997 B1 | 11/2008 | Pianca et al. |
| 7,596,414 B2 | 9/2009 | Whitehurst et al. |
| 7,610,103 B2 | 10/2009 | Whitehurst et al. |
| 7,672,734 B2 | 3/2010 | Anderson et al. |
| 7,684,869 B2 | 3/2010 | Bradley et al. |
| 7,736,382 B2 | 6/2010 | Webb et al. |
| 7,761,165 B1 | 7/2010 | He et al. |
| 7,783,359 B2 | 8/2010 | Meadows |
| 7,792,590 B1 | 9/2010 | Pianca et al. |
| 7,803,021 B1 | 9/2010 | Brase |
| 7,809,435 B1 | 10/2010 | Ettare et al. |
| 7,809,446 B2 | 10/2010 | Meadows |
| 7,946,980 B2 | 5/2011 | Reddy et al. |
| 7,949,395 B2 | 5/2011 | Kuzma |
| 7,949,409 B2 | 5/2011 | Bly et al. |
| 7,974,706 B2 | 7/2011 | Moffitt et al. |
| 8,086,322 B2 | 12/2011 | Schouenborg |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,311,647 B2 | 11/2012 | Bly |
| 8,326,433 B2 | 12/2012 | Blum et al. |
| 8,340,785 B2 | 12/2012 | Bonde et al. |
| 8,364,278 B2 | 1/2013 | Pianca et al. |
| 8,386,054 B2 | 2/2013 | North |
| 8,391,985 B2 | 3/2013 | McDonald |
| 8,463,343 B2 | 6/2013 | Kuhn et al. |
| 8,473,061 B2 | 6/2013 | Moffitt et al. |
| 8,483,237 B2 | 7/2013 | Zimmermann et al. |
| 8,525,027 B2 | 9/2013 | Lindner et al. |
| 8,571,665 B2 | 10/2013 | Moffitt et al. |
| 8,600,509 B2 | 12/2013 | McDonald et al. |
| 8,675,945 B2 | 3/2014 | Barnhorst et al. |
| 8,682,439 B2 | 3/2014 | DeRohan et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,831,742 B2 | 9/2014 | Pianca et al. |
| 8,831,746 B2 | 9/2014 | Swanson |
| 8,849,632 B2 | 9/2014 | Sparks et al. |
| 8,855,768 B1 | 10/2014 | Johnson et al. |
| 8,868,211 B2 | 10/2014 | Durand et al. |
| 8,897,876 B2 | 11/2014 | Sundaramurthy et al. |
| 8,929,973 B1 | 1/2015 | Webb et al. |
| 8,936,630 B2 | 1/2015 | Denison et al. |
| 8,958,615 B2 | 2/2015 | Blum et al. |
| 9,238,132 B2 | 1/2016 | Barker |
| 9,409,032 B2 | 8/2016 | Brase et al. |
| 9,415,154 B2 | 8/2016 | Leven |
| 9,421,362 B2 | 8/2016 | Seeley |
| 9,440,066 B2 | 9/2016 | Black |
| 9,550,063 B2 | 1/2017 | Wolf, II |
| 9,604,068 B2 | 3/2017 | Malinowski |
| 9,643,010 B2 | 5/2017 | Ranu |
| 9,656,093 B2 | 5/2017 | Villarta et al. |
| 9,681,809 B2 | 6/2017 | Sharma et al. |
| 9,770,598 B2 | 9/2017 | Malinowski et al. |
| 9,931,511 B2 | 4/2018 | Kaula et al. |
| 10,213,596 B2 | 2/2019 | Orinski |
| 10,307,602 B2 | 6/2019 | Leven |
| 10,335,607 B2 | 7/2019 | Orinski |
| 10,471,273 B2 | 11/2019 | Segev et al. |
| 10,625,072 B2 | 4/2020 | Serrano Carmona |
| 10,644,194 B2 | 5/2020 | Kim et al. |
| 10,814,140 B2 | 10/2020 | Zhang et al. |
| 11,395,923 B2 | 7/2022 | Lu et al. |
| 2002/0156513 A1 | 10/2002 | Borkan |
| 2002/0161417 A1 | 10/2002 | Scribner |
| 2004/0073278 A1 | 4/2004 | Pachys |
| 2004/0098063 A1 | 5/2004 | Goetz |
| 2004/0147964 A1 | 7/2004 | Nolan et al. |
| 2005/0216072 A1 | 9/2005 | Mahadevan-Jansen et al. |
| 2006/0129210 A1 | 6/2006 | Cantin et al. |
| 2006/0155348 A1 | 7/2006 | deCharms |
| 2006/0161227 A1 | 7/2006 | Walsh, Jr. et al. |
| 2007/0053996 A1 | 3/2007 | Boyden et al. |
| 2007/0100398 A1 | 5/2007 | Sloan |
| 2007/0150036 A1 | 6/2007 | Anderson |
| 2007/0161919 A1 | 7/2007 | DiLorenzo |
| 2007/0208395 A1 | 9/2007 | Leclerc et al. |
| 2007/0244524 A1 | 10/2007 | Qu et al. |
| 2007/0244526 A1 | 10/2007 | Zaghetto et al. |
| 2008/0046053 A1 | 2/2008 | Wagner et al. |
| 2008/0077198 A1 | 3/2008 | Webb et al. |
| 2008/0146890 A1 | 6/2008 | LeBouef et al. |
| 2008/0167701 A1 | 7/2008 | John et al. |
| 2008/0197300 A1 | 8/2008 | Kayser et al. |
| 2008/0243218 A1 | 10/2008 | Bottomley et al. |
| 2009/0054954 A1 | 2/2009 | Foley et al. |
| 2009/0054955 A1 | 2/2009 | Kopell et al. |
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0196471 A1 | 8/2009 | Goetz et al. |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2009/0299447 A1 | 12/2009 | Jensen et al. |
| 2010/0076508 A1 | 3/2010 | McDonald et al. |
| 2010/0076535 A1 | 3/2010 | Pianca et al. |
| 2010/0094364 A1 | 4/2010 | McDonald |
| 2010/0105997 A1 | 4/2010 | Ecker et al. |
| 2010/0114190 A1 | 5/2010 | Bendett et al. |
| 2010/0174329 A1 | 7/2010 | Dadd et al. |
| 2010/0174344 A1 | 7/2010 | Dadd et al. |
| 2010/0256693 A1 | 10/2010 | McDonald et al. |
| 2010/0268298 A1 | 10/2010 | Moffitt et al. |
| 2010/0292758 A1 | 11/2010 | Lee et al. |
| 2010/0292759 A1 | 11/2010 | Hahn et al. |
| 2010/0324630 A1 | 12/2010 | Lee et al. |
| 2010/0326701 A1 | 12/2010 | McDonald |
| 2011/0004267 A1 | 1/2011 | Meadows |
| 2011/0005069 A1 | 1/2011 | Pianca |
| 2011/0009932 A1 | 1/2011 | McDonald et al. |
| 2011/0022100 A1 | 1/2011 | Brase et al. |
| 2011/0029055 A1 | 2/2011 | Tidemand |
| 2011/0046432 A1 | 2/2011 | Simon et al. |
| 2011/0046700 A1 | 2/2011 | McDonald et al. |
| 2011/0078900 A1 | 4/2011 | Pianca et al. |
| 2011/0106208 A1 | 5/2011 | Faltys et al. |
| 2011/0112591 A1 | 5/2011 | Seymour et al. |
| 2011/0125077 A1 | 5/2011 | Denison et al. |
| 2011/0125078 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |

(56) References Cited

U.S. PATENT DOCUMENTS

| | | |
|---|---|---|
| 2011/0130818 A1 | 6/2011 | Chen |
| 2011/0172653 A1 | 7/2011 | Schneider et al. |
| 2011/0172725 A1 | 7/2011 | Wells et al. |
| 2011/0238129 A1 | 9/2011 | Moffitt et al. |
| 2011/0295331 A1 | 12/2011 | Wells et al. |
| 2011/0313500 A1 | 12/2011 | Barker et al. |
| 2012/0014580 A1 | 1/2012 | Blum et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0232354 A1 | 9/2012 | Ecker et al. |
| 2012/0253261 A1 | 10/2012 | Poletto et al. |
| 2012/0265262 A1 | 10/2012 | Osorio |
| 2012/0265268 A1 | 10/2012 | Blum et al. |
| 2012/0287420 A1 | 11/2012 | Mclaughlin et al. |
| 2012/0314924 A1 | 12/2012 | Carlton et al. |
| 2012/0316615 A1 | 12/2012 | Digiore et al. |
| 2012/0319010 A1 | 12/2012 | Bornstein et al. |
| 2013/0019325 A1 | 1/2013 | Deisseroth et al. |
| 2013/0053905 A1 | 2/2013 | Wagner |
| 2013/0079848 A1 | 3/2013 | Campbell et al. |
| 2013/0102861 A1 | 4/2013 | Oki et al. |
| 2013/0105071 A1 | 5/2013 | Digiore et al. |
| 2013/0116744 A1 | 5/2013 | Blum et al. |
| 2013/0184794 A1 | 7/2013 | Feldman et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0281819 A1 | 10/2013 | Schmid |
| 2013/0304152 A1 | 11/2013 | Bradley et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067015 A1 | 3/2014 | Kothandaraman et al. |
| 2014/0067023 A1 | 3/2014 | Register et al. |
| 2014/0074182 A1 | 3/2014 | Wolf, II |
| 2014/0114150 A1 | 4/2014 | Pogue et al. |
| 2014/0122379 A1 | 5/2014 | Moffitt et al. |
| 2014/0142664 A1 | 5/2014 | Roukes et al. |
| 2014/0163639 A1 | 6/2014 | Zhu |
| 2014/0200639 A1 | 7/2014 | De La Rama |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005680 A1 | 1/2015 | Lipani |
| 2015/0005860 A1 | 1/2015 | Howard et al. |
| 2015/0018915 A1 | 1/2015 | Leven |
| 2015/0021817 A1 | 1/2015 | Romero et al. |
| 2015/0045862 A1 | 2/2015 | Goldman et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0080757 A1 | 3/2015 | Torisawa et al. |
| 2015/0151113 A1 | 6/2015 | Govea et al. |
| 2015/0202456 A1 | 7/2015 | Andersen et al. |
| 2015/0290461 A1 | 10/2015 | Min et al. |
| 2015/0306414 A1 | 10/2015 | Nielsen et al. |
| 2015/0360031 A1 | 12/2015 | Bornzin et al. |
| 2015/0375006 A1 | 12/2015 | Denison et al. |
| 2016/0030749 A1 | 2/2016 | Carcieri et al. |
| 2016/0045740 A1 | 2/2016 | Rezai et al. |
| 2016/0067519 A1 | 3/2016 | Tranberg et al. |
| 2016/0082251 A1 | 3/2016 | Moffitt et al. |
| 2016/0082253 A1 | 3/2016 | Moffitt et al. |
| 2016/0151639 A1* | 6/2016 | Scharf ............... A61N 5/0624 607/92 |
| 2016/0228692 A1 | 8/2016 | Steinke et al. |
| 2016/0250474 A1 | 9/2016 | Stack et al. |
| 2016/0250497 A1 | 9/2016 | Jay |
| 2016/0256689 A1 | 9/2016 | Vallejo et al. |
| 2016/0271392 A1 | 9/2016 | Vallejo et al. |
| 2016/0271413 A1 | 9/2016 | Vallejo et al. |
| 2016/0287885 A1 | 10/2016 | Saini |
| 2016/0296745 A1 | 10/2016 | Govea et al. |
| 2016/0331994 A1 | 11/2016 | Smith et al. |
| 2016/0346557 A1 | 12/2016 | Bokil |
| 2016/0361543 A1 | 12/2016 | Kaula et al. |
| 2016/0375258 A1 | 12/2016 | Steinke |
| 2017/0000419 A1 | 1/2017 | Schouenborg |
| 2017/0061627 A1 | 3/2017 | Bokil |
| 2017/0095670 A1 | 4/2017 | Ghaffari et al. |
| 2017/0100580 A1 | 4/2017 | Olson |
| 2017/0136254 A1 | 5/2017 | Simon et al. |
| 2017/0143985 A1 | 5/2017 | Degenaar et al. |
| 2017/0172446 A1 | 6/2017 | Kuzum et al. |
| 2017/0182191 A1* | 6/2017 | Towne ............... A61K 48/0075 |
| 2017/0225007 A1 | 8/2017 | Orinski |
| 2017/0259078 A1 | 9/2017 | Howard |
| 2017/0281928 A1 | 10/2017 | Orinski |
| 2017/0281966 A1 | 10/2017 | Basiony |
| 2017/0304633 A1 | 10/2017 | Zhang |
| 2017/0348522 A1 | 12/2017 | Stoffregen et al. |
| 2017/0361108 A1 | 12/2017 | Leven |
| 2017/0361122 A1 | 12/2017 | Chabrol et al. |
| 2018/0028820 A1 | 2/2018 | Nageri |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Serrano Carmona |
| 2018/0154152 A1 | 6/2018 | Chabrol et al. |
| 2018/0193655 A1 | 7/2018 | Zhang et al. |
| 2018/0229042 A1 | 8/2018 | Kaula et al. |
| 2018/0243570 A1 | 8/2018 | Malinowski et al. |
| 2018/0256906 A1 | 9/2018 | Pivonka et al. |
| 2018/0318578 A1 | 11/2018 | Ng et al. |
| 2018/0326219 A1 | 11/2018 | Wolf, II |
| 2018/0369606 A1 | 12/2018 | Zhang et al. |
| 2018/0369607 A1 | 12/2018 | Zhang et al. |
| 2018/0369608 A1 | 12/2018 | Chabrol |
| 2019/0003898 A1 | 1/2019 | Dehkhoda et al. |
| 2019/0201709 A1 | 7/2019 | Tischendorf et al. |
| 2019/0209834 A1 | 7/2019 | Zhang et al. |
| 2019/0209849 A1 | 7/2019 | Hershey et al. |
| 2019/0209850 A1 | 7/2019 | Steinke |
| 2020/0001096 A1 | 1/2020 | Zhang et al. |
| 2020/0094047 A1 | 3/2020 | Govea et al. |
| 2020/0155584 A1 | 5/2020 | DiMauro |
| 2020/0155854 A1 | 5/2020 | Leven et al. |
| 2020/0271796 A1 | 8/2020 | Tahon et al. |
| 2020/0323589 A1 | 10/2020 | Varol |
| 2020/0376262 A1 | 12/2020 | Clark et al. |
| 2020/0376272 A1 | 12/2020 | Block et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |
| 2021/0178175 A1 | 6/2021 | Chabrol et al. |
| 2021/0389175 A1* | 12/2021 | Leblanc ............... G02B 5/0284 |
| 2022/0054226 A1 | 2/2022 | Gregg, II et al. |
| 2022/0072329 A1 | 3/2022 | Howard |
| 2022/0111212 A1 | 4/2022 | Howard |
| 2022/0266000 A1 | 8/2022 | Moffitt |
| 2022/0323781 A1 | 10/2022 | Subramanian et al. |
| 2022/0339448 A1 | 10/2022 | Jayakumar et al. |
| 2024/0001141 A1 | 1/2024 | Bruhat et al. |
| 2024/0058619 A1 | 2/2024 | Zhu et al. |

(56) References Cited

U.S. PATENT DOCUMENTS

2024/0198128 A1    6/2024    Jenkins et al.
2024/0226596 A1    7/2024    Carbunaru et al.

FOREIGN PATENT DOCUMENTS

| | | |
|---|---|---|
| EP | 30204501 A1 | 5/2016 |
| KR | 20220143523 A | 10/2022 |
| WO | 02/091935 | 11/2002 |
| WO | 2010029297 | 3/2010 |
| WO | 2011/031131 | 3/2011 |
| WO | 2011150430 | 12/2011 |
| WO | WO2012024243 A1 | 2/2012 |
| WO | 2012/103543 | 8/2012 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |
| WO | 2021141163 | 7/2021 |

OTHER PUBLICATIONS

Baxter, G.D. et al., Effects of Low Intensity Infrared Laser Irradiation Upon Conduction in the Human Median Nerve In Vivo, Experimental Physiology (1994) 79, 227-234.

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.

Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.

Use of NAD(P)H and flavoprotein autofluorescence transients to probe neuron and astrocyte responses to synaptic activation. Shuttleworth 2010 Neurochemestry international.

Vallejo, Ricardo, Kerry Bradley, and Leonardo Kapural. "Spinal cord stimulation in chronic pain: Mode of action." Spine 42 (2017): S53-S60.

Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.

R G Wilson, "Ball-lens coupling efficiency for laser-diode to single-mode fiber: comparison of independent studies by distinct methods," Applied Optics May 20, 1998, 37 (15): 3201-5.

U.S. Appl. No. 18/232,621, filed Aug. 10, 2023.

U.S. Appl. No. 18/232,649, filed Aug. 10, 2023.

Weiran Cao, Jian Li, Hongzheng Chen, Jiangeng Xue, "Transparent electrodes for organic optoelectronic devices: a review," J. Photon. Energy 4(1) 040990 (Oct. 30, 2014) https://doi.org/10.1117/1.JPE.4.040990.

Lee KT, Park DH, Baac HW, Han S. Graphene- and Carbon-Nanotube-Based Transparent Electrodes for Semitransparent Solar Cells. Materials (Basel). Aug. 22, 2018;11(9):1503. doi: 10.3390/ma11091503. PMID: 30135379; PMCID: PMC6165141.

* cited by examiner

SYSTEMS AND METHODS INCORPORATING A LIGHT THERAPY USER INTERFACE FOR OPTICAL MODULATION

CROSS-REFERENCE TO RELATED APPLICATIONS

This application claims the benefit under 35 U.S.C. § 119(e) of U.S. Provisional Patent Application Ser. No. 63/437,050, filed Jan. 4, 2023, which is incorporated herein by reference.

FIELD

The present invention is directed to the area of implantable optical modulation systems and methods of making and using the systems. The present invention is also directed to systems and methods for visualizing and controlling optical modulation using optical modulation leads and systems, as well as user interfaces for optical modulation systems.

BACKGROUND

Implantable optical modulation systems can provide therapeutic benefits in a variety of diseases and disorders. For example, optical modulation can be applied to the brain either externally or using an implanted modulation lead to provide, for example, deep brain modulation, to treat a variety of diseases or disorders. Optical modulation may also be combined with electrical stimulation.

Stimulators have been developed to provide therapy for a variety of treatments. A stimulator can include a control module (for generating light or electrical signals sent to light sources in a lead), one or more leads, and one or more light sources coupled to, or disposed within, each lead. The lead is positioned near the nerves, muscles, or other tissue to be stimulated.

BRIEF SUMMARY

One aspect is an optical modulation system that includes a display; a memory including instructions; a processor coupled to the display and the memory and configured to execute the instructions, wherein the instructions include presenting, on the display, a user interface including a plurality of user-selectable controls to select or adjust values for each of a plurality of modulation parameters; receiving a target; receiving or determining a location of an optical modulation lead relative to the target; presenting, on the display, a representation of the optical modulation lead and a representation of the target relative to the location of the optical modulation lead; estimating a modulation dosage or irradiance at the target based on, at least, the target, the location of the optical modulation lead, the values of the modulation parameters, and estimated light attenuation by tissue between the optical modulation lead and the target; and presenting, on the display, a value of the estimated modulation dosage or irradiance at the target.

Another aspect is a method for optical modulation or programming optical modulation. The method includes presenting, on a display, a user interface including a plurality of user-selectable controls to select or adjust values for each of a plurality of modulation parameters; receiving a target; receiving or determining a location of an optical modulation lead relative to the target; presenting, on the display, a representation of the optical modulation lead and a representation of the target relative to the location of the optical modulation lead; estimating a modulation dosage or irradiance at the target based on, at least, the target, the location of the optical modulation lead, the values of the modulation parameters, and estimated light attenuation by tissue between the optical modulation lead and the target; and presenting, on the display, a value of the estimated modulation dosage or irradiance at the target.

Yet another aspect is a non-transitory computer readable medium have instructions stored thereon, wherein the instructions include presenting, on a display, a user interface including a plurality of user-selectable controls to select or adjust values for each of a plurality of modulation parameters; receiving a target; receiving or determining a location of an optical modulation lead relative to the target; presenting, on the display, a representation of the optical modulation lead and a representation of the target relative to the location of the optical modulation lead; estimating a modulation dosage or irradiance at the target based on, at least, the target, the location of the optical modulation lead, the values of the modulation parameters, and estimated light attenuation by tissue between the optical modulation lead and the target; and presenting, on the display, a value of the estimated modulation dosage or irradiance at the target.

In at least some aspects, the instructions or method further include presenting, on the display, a pointer, and the value of the estimated modulation dosage or irradiance at the site of the pointer relative to the representation of the lead. In at least some aspects, the value of the modulation dosage or irradiance at the target is an instantaneous value of the irradiance at the target. In at least some aspects, the value of the modulation dosage or irradiance at the target is a value of the modulation dosage or irradiance delivered at the target over a defined area. In at least some aspects, the value of the modulation dosage or irradiance at the target is a cumulative value of the modulation dosage delivered at the target for a selected period of time. In at least some aspects, the value of the modulation dosage or irradiance at the target is a value of the modulation dosage delivered at the target for a predefined modulation dosage period.

In at least some aspects, the instructions or method further include presenting, on the display, a representation of an estimated light distribution. In at least some aspects, presenting the representation of the estimated light distribution includes presenting the representation of the estimated light distribution using a plurality of colors, a plurality of shades, or at least one contour line to delineate regions based on a) an estimated amount of irradiance or modulation dosage received in each of the regions or b) an estimated temperature or temperature change for each of the regions. In at least some aspects, the location of the optical modulation lead comprises the location of at least one light emitter of the optical modulation lead.

A further aspect is an optical modulation system that includes a display; a memory including instructions; a processor coupled to the display and the memory and configured to execute the instructions, wherein the instructions include presenting, on the display, a user interface including a plurality of user-selectable controls to select or adjust values for each of a plurality of modulation parameters; receiving a target; receiving or determining a location of an optical modulation lead relative to the target; receiving a selection of the value for each of a plurality of the modulation parameters; and estimating a modulation dosage at the target based on, at least, the target, the location of the optical modulation lead, and the selected values of the modulation parameters, and at least one of a) estimated light attenuation by tissue between the optical modulation lead and the target or b) estimated light distribution with the tissue.

Another aspect is a method for optical modulation or programming optical modulation. The method includes presenting, on a display, a user interface including a plurality of user-selectable controls to select or adjust values for each of a plurality of modulation parameters; receiving a target; receiving or determining a location of an optical modulation lead relative to the target; receiving a selection of the value for each of a plurality of the modulation parameters; and estimating a modulation dosage at the target based on, at least, the target, the location of the optical modulation lead, and the selected values of the modulation parameters, and at least one of a) estimated light attenuation by tissue between the optical modulation lead and the target or b) estimated light distribution with the tissue.

Yet another aspect is a non-transitory computer readable medium having instructions stored thereon, wherein the instructions include presenting, on a display, a user interface including a plurality of user-selectable controls to select or adjust values for each of a plurality of modulation parameters; receiving a target; receiving or determining a location of an optical modulation lead relative to the target; receiving a selection of the value for each of a plurality of the modulation parameters; and estimating a modulation dosage at the target based on, at least, the target, the location of the optical modulation lead, and the selected values of the modulation parameters, and at least one of a) estimated light attenuation by tissue between the optical modulation lead and the target or b) estimated light distribution with the tissue.

In at least some aspects, the instructions or method further include presenting, on the display, a representation of the optical modulation lead and a representation of the target relative to the location of the optical modulation lead. In at least some aspects, the instructions or method further include presenting, on the display, a value of the estimated modulation dosage at the target.

In at least some aspects, the instructions or method further include presenting, on the display, a representation of an estimated light distribution. In at least some aspects, presenting the representation of the estimated light distribution includes presenting the representation of the estimated light distribution using a plurality of colors, a plurality of shades, or at least one contour line to delineate regions based on a) an estimated amount of irradiance or modulation dosage received in each of the regions or b) an estimated temperature or temperature change for each of the regions.

A further aspect is an optical modulation system that includes a display; a memory including instructions; a processor coupled to the display and the memory and configured to execute the instructions, wherein the instructions include presenting, on the display, a user interface including a plurality of user-selectable controls to select or adjust values for each of a plurality of modulation parameters; receiving a target; receiving or determining a location of an optical modulation lead relative to the target; and receiving a selection of the value for each of a plurality of the modulation parameters, wherein the selection of the value of at least one of the modulation parameters is limited by at least one of a) an estimation, by the processor, of a modulation dosage, temperature change, temperature, heating, or delivered energy at the target based on, at least, the target, the location of the optical modulation lead, and the selected value of at least one other of the modulation parameters or b) an estimation, by the processor, of a dosage, temperature change, temperature, heating, or delivered energy at non-target tissue based on, at least, a location of the non-target tissue, a threshold value, the location of the optical modulation lead, and the selected value of at least one other of the modulation parameters.

Another aspect is a method for optical modulation or programming optical modulation. The method includes presenting, on a display, a user interface including a plurality of user-selectable controls to select or adjust values for each of a plurality of modulation parameters; receiving a target; receiving or determining a location of an optical modulation lead relative to the target; and receiving a selection of the value for each of a plurality of the modulation parameters, wherein the selection of the value of at least one of the modulation parameters is limited by at least one of a) an estimation, by the processor, of a modulation dosage, temperature change, temperature, heating, or delivered energy at the target based on, at least, the target, the location of the optical modulation lead, and the selected value of at least one other of the modulation parameters or b) an estimation, by the processor, of a dosage, temperature change, temperature, heating, or delivered energy at non-target tissue based on, at least, a location of the non-target tissue, a threshold value, the location of the optical modulation lead, and the selected value of at least one other of the modulation parameters.

Yet another aspect is a non-transitory computer readable medium having instructions stored thereon, wherein the instructions include presenting, on a display, a user interface including a plurality of user-selectable controls to select or adjust values for each of a plurality of modulation parameters; receiving a target; receiving or determining a location of an optical modulation lead relative to the target; and receiving a selection of the value for each of a plurality of the modulation parameters, wherein the selection of the value of at least one of the modulation parameters is limited by at least one of a) an estimation, by the processor, of a modulation dosage, temperature change, temperature, heating, or delivered energy at the target based on, at least, the target, the location of the optical modulation lead, and the selected value of at least one other of the modulation parameters or b) an estimation, by the processor, of a dosage, temperature change, temperature, heating, or delivered energy at non-target tissue based on, at least, a location of the non-target tissue, a threshold value, the location of the optical modulation lead, and the selected value of at least one other of the modulation parameters.

In at least some aspects, the value of the at least one of the modulation parameters that is limited is the value of the modulation intensity. In at least some aspects, the estimation of the modulation dosage is an estimation of the modulation dosage over a predefined modulation dosage period. In at least some aspects, the estimation of the dosage, temperature change, temperature, heating, or delivered energy at the non-target tissue is an estimation of the dosage, temperature change, temperature, heating, or delivered energy over a predefined period of time. In at least some aspects, the value of the at least one of the modulation parameters is limited when the estimation of the modulation dosage or the estimation of the dosage, temperature change, temperature, heating, or delivered energy exceeds a preselected value.

In at least some aspects, the instructions or method further include presenting, on the display, a representation of an estimated light distribution. In at least some aspects, presenting the representation of the estimated light distribution includes presenting the representation of the estimated light distribution using a plurality of colors, a plurality of shades, or at least one contour line to delineate regions based on an estimated amount of irradiance or modulation dosage received in each of the regions. In at least some aspects, presenting the representation of the estimated light distribution includes presenting the representation of the estimated light distribution using a plurality of colors, a plurality of shades, or at least one contour line to delineate regions based on an estimated temperature or temperature change for each of the regions.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable optical modulation systems and methods of making and using the systems. The present invention is also directed to systems and methods for visualizing and controlling optical modulation using optical modulation leads and systems, as well as user interfaces for optical modulation systems.

In some embodiments, an implantable optical modulation system only provides optical modulation. Examples of optical modulation systems with leads are found in, for example, U.S. Pat. Nos. 9,415,154; 10,335,607; 10,625,072; and 10,814,140 and U.S. Patent Applications Publication Nos. 2020/0155584; 2020/0376272; 2021/0008388; 2021/0008389; 2021/0016111; and 2022/0072329, all of which are incorporated by reference in their entireties.

In other embodiments, the system can provide both optical modulation and electrical stimulation. In at least some of these embodiments, the optical modulation system can be a modification of an electrical stimulation system to also provide optical modulation. Suitable implantable electrical stimulation systems that can be modified to also provide optical modulation include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761, 165; 7,783,359; 7,792,590; 7,809,435; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties.

Figure 1:
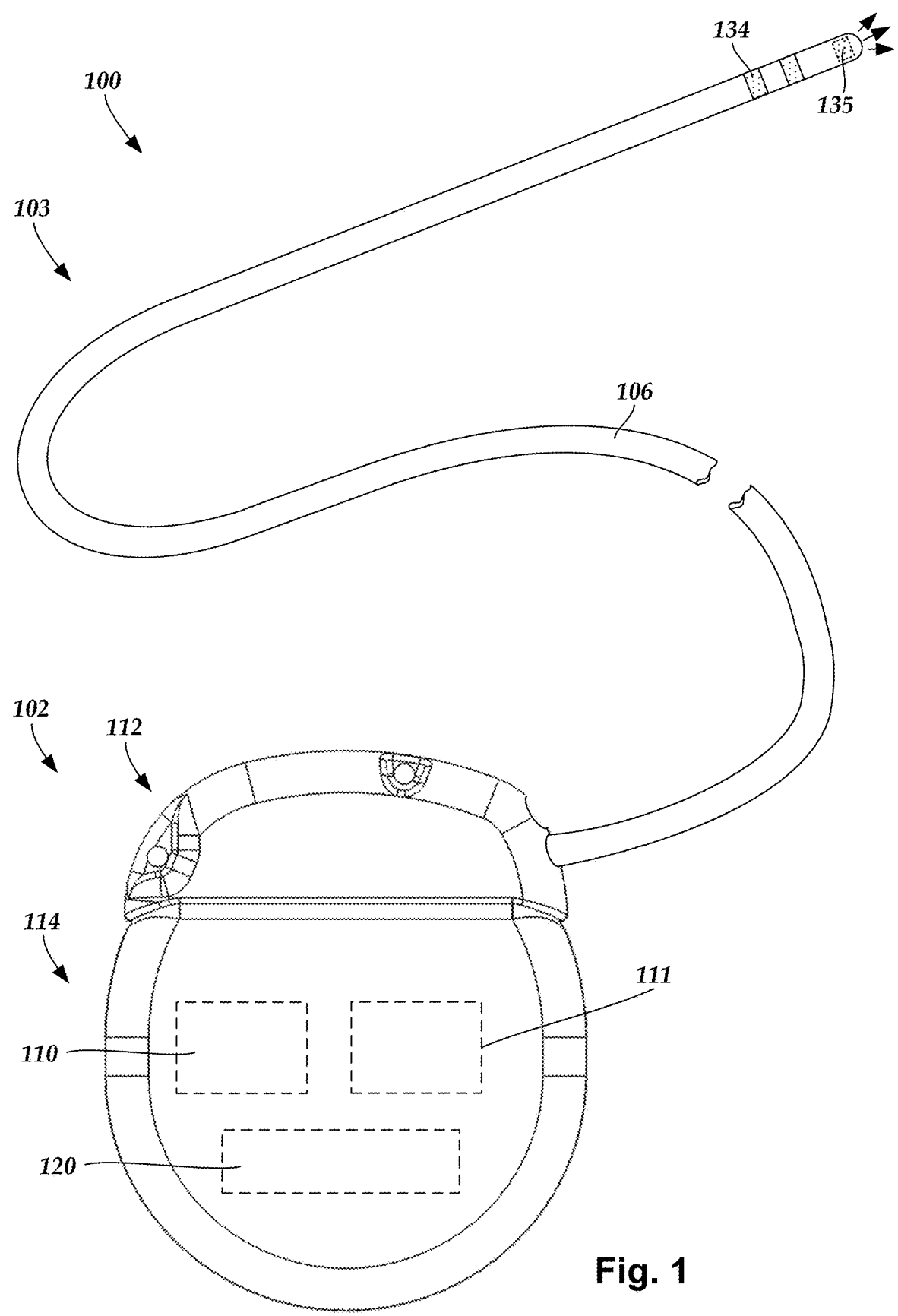
FIG. 1 is a schematic side view of one embodiment of an optical modulation system that includes a lead coupled to a control module.
Figure 2A:
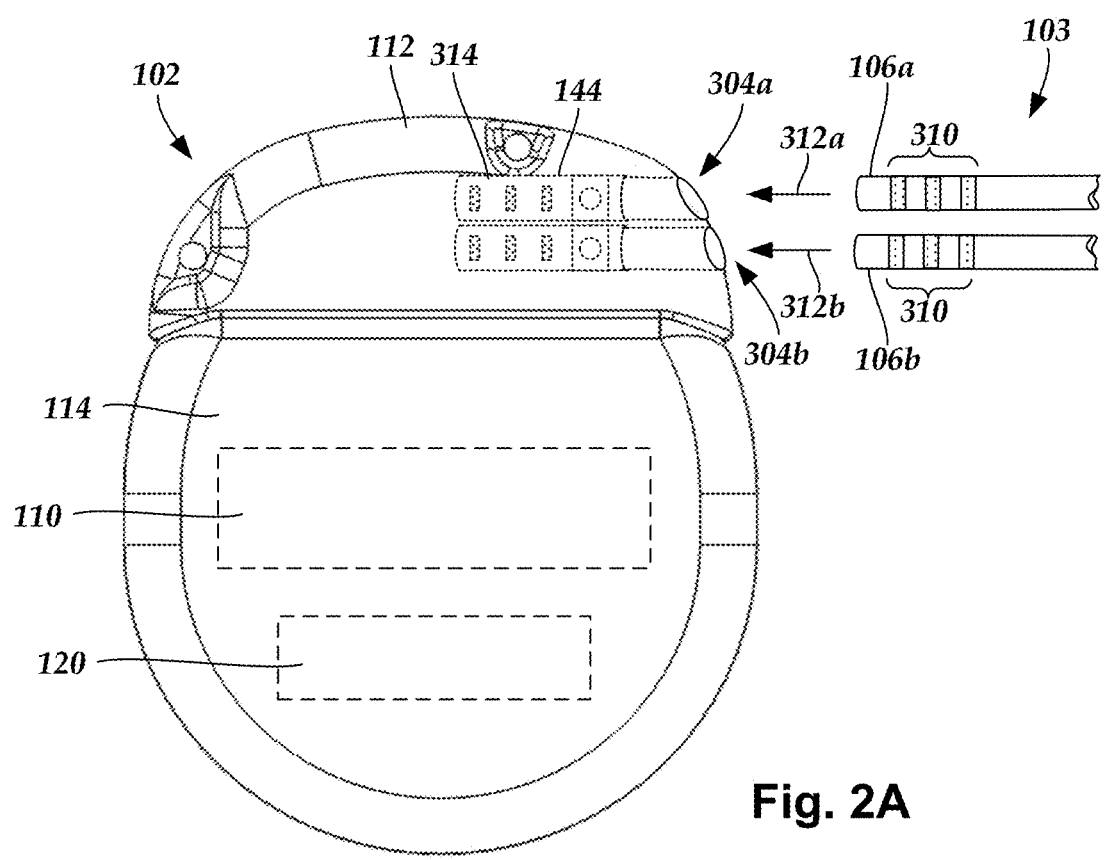
FIG. 2A is a schematic side view of one embodiment of the control module of FIG. 1 configured and arranged to couple to an elongated device.

FIG. 1 illustrates schematically one embodiment of an optical modulation system 100. The optical modulation system includes a control module (e.g., a stimulator) 102 and a lead 103 coupleable to the control module 102. The lead 103 includes one or more lead bodies 106. In FIG. 1, the lead 103 is shown having a single lead body 106. In FIG. 2A, the lead 103 includes two lead bodies 106a, 106b. It will be understood that the lead 103 can include any suitable number of lead bodies including, for example, one, two, three, four, five, six, seven, eight or more lead bodies 106.

At least one light emitter 135 is provided along a distal portion of the lead 103. The light emitter 135 can be a light source, such as a light-emitting diode ("LED"), laser diode, organic light-emitting diode ("OLED"), or the like, or can be a terminus of a light transmission element, such as an optical fiber, fiber optic, optical waveguide, or the like, in which case the light source is distant from the distal portion of the lead (for example, in the control module or in a proximal portion of the lead). The lead can also include optional electrodes 134 disposed along the lead body 106, and one or more terminals 310 (FIGS. 2A-2B) disposed along each of the one or more lead bodies 106 and coupled to the electrodes 134 by conductors (not shown). In at least some embodiments, one or more terminals 310 (FIGS. 2A-2B) may also be used to convey electrical signals to a light source that acts as the light emitter 135 by conductors (not shown) extending along the lead.

The optional electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, iridium, iridium oxide, palladium rhodium, or titanium. In at least some embodiments, at least one of the electrodes 134 is formed from an optically-transparent material. Any suitable number of electrodes 134 can be disposed on the lead including, for example, one, two, three, four, five, six, seven, eight, nine, ten, eleven, twelve, fourteen, sixteen, twenty-four, thirty-two, or more electrodes 134.

Figure 2B:
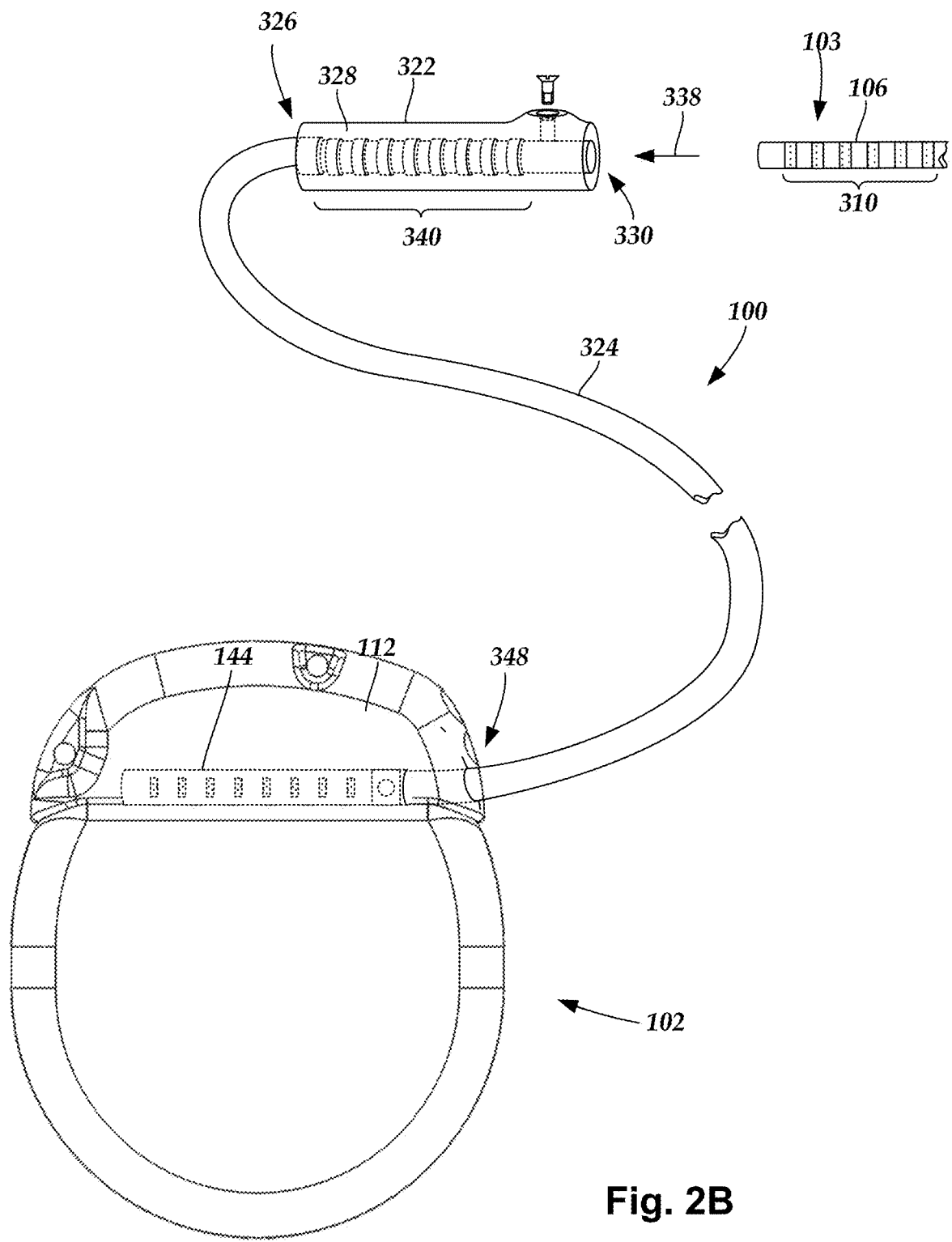
FIG. 2B is a schematic side view of one embodiment of a lead extension configured and arranged to couple the elongated device of FIG. 2A to the control module of FIG. 1.

The lead 103 can be coupled to the control module 102 in any suitable manner. In some embodiments, the lead is permanently attached to the control module 102. In other embodiments, the lead can be coupled to the control module 102 by a connector 144 (FIG. 2A). In FIG. 2A, the lead 103 is shown coupling directly to the control module 102 through the connector 144. In at least some other embodiments, the lead 103 couples to the control module 102 via one or more intermediate devices, as illustrated in FIG. 2B. For example, in at least some embodiments, one or more lead extensions 324 (FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the optical modulation system 100 includes multiple elongated devices disposed between the lead 103 and the control module 102, the intermediate devices may be configured into any suitable arrangement.

The control module 102 can include, for example, a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

In some embodiments, the control module 102 also includes one or more light sources 111 disposed within the sealed electronics housing 114. In alternate embodiments, the one or more light sources 111 are external to the control module. The one or more light sources can be, for example, a light-emitting diode ("LED"), laser diode, organic light-emitting diode ("OLED"), or the like. When the control module 102 includes multiple light sources, the light sources can provide light in at a same wavelength or wavelength band or some, or all, of the light sources can provide light at different wavelength or different wavelength bands. When the one or more light sources 111 are external to the lead(s), the light emitted by the light sources can be directed to one or more optical fibers, fiber optics, optical waveguides, or the like. The optical fiber, or a series of optical fibers, can transmit the light from the one or more light sources 111 through the control module 102 and lead 103 to the light emitter 135 (which can be terminus of the optical fiber). In at least some embodiments, the optical fiber is a single mode optical fiber. In other embodiments, the optical fiber is a multi-mode optical fiber. In some embodiments, the system includes a single optical fiber. In other embodiments, the system may employ multiple optical fibers in series or in parallel.

In other embodiments, the light emitter 135 can also be the light source, or a combination of light sources, with conductors extending along the lead 103 and coupled to the electronic subassembly 110 to provide signals and power for operating the light source. In yet other embodiments, the light source can be disposed elsewhere in the control module 102, on the lead 103, in another element such as a lead extension, splitter, adaptor, or other stand-alone element.

The optical modulation system or components of the optical modulation system, including the lead 103 and the control module 102, are typically implanted into the body of a patient. The optical modulation system can be used for a variety of applications including, but not limited to brain modulation, deep brain modulation, neural modulation, spinal cord modulation, muscle modulation, sacral nerve modulation, dorsal root ganglion modulation, peripheral nerve modulation, and the like.

The one or more lead bodies 106 are made of a non-conductive, biocompatible material such as, for example, silicone, polyurethane, polyether ether ketone ("PEEK"), epoxy, and the like or combinations thereof. The one or more lead bodies 106 may be formed in the desired shape by any process including, for example, molding (including injection molding), casting, and the like.

One or more terminals 310 (FIGS. 2A-2B) are typically disposed along the proximal end of the one or more lead bodies 106 of the optical modulation system 100 (as well as any splitters, lead extensions, adaptors, or the like) for electrical connection to corresponding connector contacts (e.g., 314 in FIGS. 2A-2B). The connector contacts are disposed in connectors (for example, 144 in FIGS. 1-2B; and 322 FIG. 2B) which, in turn, are disposed on, for example, the control module 102 (or a lead extension, a splitter, an adaptor, or the like). Electrically conductive wires, cables, or the like (not shown) extend from the terminals to the light emitter 135 or electrodes 134.

The electrically-conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal portion of lead 103 or other elongated device configured and arranged for coupling to one embodiment of the control module connector 144. The one or more elongated devices may include, for example, one or more of the lead bodies 106 of FIG. 1, one or more intermediate devices (for example, a splitter, the lead extension 324 of FIG. 2B, an adaptor, or the like or combinations thereof), or any combination thereof.

The control module connector 144 defines at least one port into which a proximal end of the lead 103 or other elongated device can be inserted, as shown by directional arrows 312a and 312b. In FIG. 2A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the lead 103 or other elongated device is inserted into the ports 304a and 304b, the connector contacts 314 can be aligned with a plurality of terminals 310 disposed along the proximal end(s) of the lead(s) 103 or other elongated device(s) to electrically couple the control module 102 to the light emitter 135 or electrodes 134 (FIG. 1) disposed on the lead 103. Each of the terminals 310 can couple to the light emitter 135 or one or more of the electrodes 134. Examples of connectors in control modules are found in, for example, U.S. Pat. Nos. 7,244,150 and 8,224,450, which are incorporated by reference.

FIG. 2B is a schematic side view of another embodiment of the optical modulation system 100. The optical modulation system 100 includes a lead extension 324 that is configured and arranged to couple the control module 102 to one or more leads 103 or other elongated devices, such as a splitter, an adaptor, another lead extension, or the like or any combination thereof. In FIG. 2B, the lead extension 324 is shown coupled to a single port 304 defined in the control module connector 144. Additionally, the lead extension 324 is shown configured and arranged to couple to a single lead 103 or other elongated device. In alternate embodiments, the lead extension 324 is configured and arranged to couple to multiple ports 304 defined in the control module connector 144 (for example, the ports 304a and 304b of FIG. 1), or to receive multiple leads 103 or other elongated devices, or both.

A lead extension connector 322 is disposed on the lead extension 324. In FIG. 2B, the lead extension connector 322 is shown disposed at a distal portion 326 of the lead extension 324. The lead extension connector 322 includes a connector housing 328. The connector housing 328 defines at least one port 330 into which terminals 310 of the lead 103 or other elongated device can be inserted, as shown by directional arrow 338. Each of the terminals 310 can couple to the light emitter 135 or one or more of the electrodes 134. The connector housing 328 also includes a plurality of connector contacts, such as connector contact 340. When the lead 103 or other elongated device is inserted into the port 330, the connector contacts 340 disposed in the connector housing 328 can be aligned with the terminals 310 of the lead 103 or other elongated device to electrically couple the lead extension 324 to the electrodes 134 (FIG. 1) or light emitter 135 (FIG. 1) disposed along the lead 103.

In at least some embodiments, the proximal end of the lead extension 324 is similarly configured and arranged as a proximal end of the lead 103 or other elongated device. The lead extension 324 may include a plurality of electrically-conductive wires (not shown) that electrically couple the connector contacts 340 to a proximal portion 348 of the lead extension 324 that is opposite to the distal portion 326. In at least some embodiments, the conductive wires disposed in the lead extension 324 can be electrically coupled to a plurality of terminals (not shown) disposed along the proximal portion 348 of the lead extension 324. In at least some embodiments, the proximal portion 348 of the lead extension 324 is configured and arranged for insertion into a connector disposed in another lead extension (or another intermediate device). In other embodiments (and as shown in FIG. 2B), the proximal portion 348 of the lead extension 324 is configured and arranged for insertion into the control module connector 144.

Figure 3:
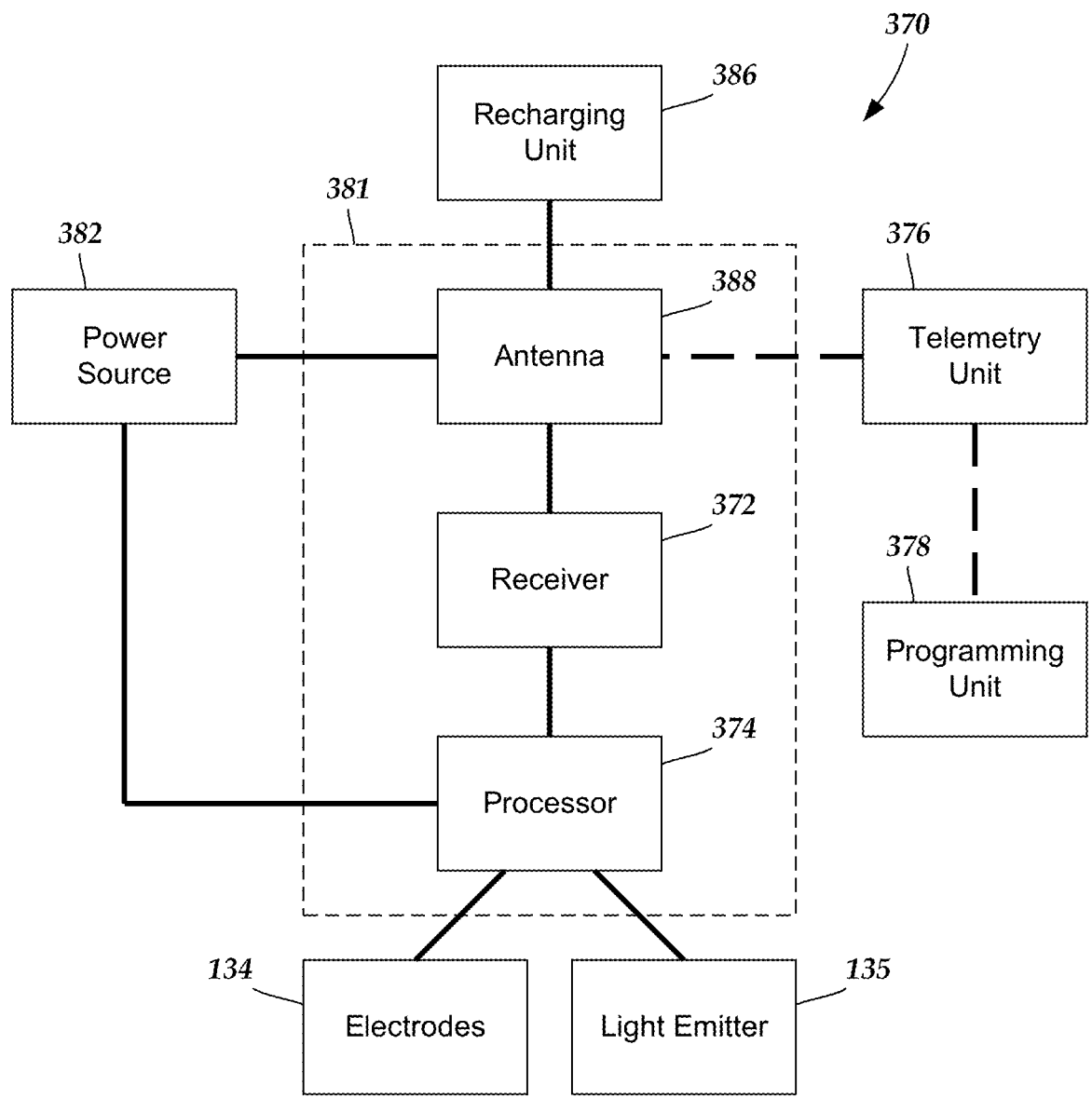
FIG. 3 is a schematic overview of one embodiment of components of an optical modulation system, including an electronic subassembly disposed within a control module.

FIG. 3 is a schematic overview of one embodiment of components of an optical modulation system 370 including an electronic subassembly 381 disposed within a control module. It will be understood that the optical modulation system can include more, fewer, or different components and can have a variety of different configurations including those configurations disclosed in the stimulator references cited herein.

Some of the components (for example, a power source 382, an antenna 388, a receiver 372, and a processor 374) of the optical modulation system can be positioned on one or more circuit boards or similar carriers within a sealed housing of an implantable pulse generator, if desired. Any power source 382 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 388 or a secondary antenna. The external power source can be in a device that is mounted on the skin of the user or in a unit that is provided near the user on a permanent or periodic basis.

If the power source 382 is a rechargeable battery, the battery may be recharged using the optional antenna 388, if desired. Power can be provided to the battery for recharging by inductively coupling the battery through the antenna to a recharging unit 386 external to the user. Examples of such arrangements can be found in the references identified above.

In one embodiment, light is emitted by the light emitter 135 of the lead body to stimulate neurons, neuronal cells, non-neuronal cells, nerve fibers, muscle fibers, or other body tissues near the optical modulation system. The processor 374 is generally included to control the timing and other characteristics of the optical modulation system. For example, the processor 374 can, if desired, control one or more of the modulation intensity, wavelength, amplitude, pulse width, pulse frequency, burst frequency, burst duration, cycling (e.g., for repeating intervals of time, determining how long to stimulate and how long to not stimulate), and electrode stimulation configuration (e.g., determining electrode polarity and fractionalization) of the optical modulation.

Additionally, the processor 374 can select which, if not all, of the sensing electrodes are activated. Moreover, the processor 394 can control which types of signals the sensing electrodes detect. In at least some embodiments, the sensing electrodes detect a level of neuronal activation, or neuronal firing rates, or both, received directly from the target modulation location. In other embodiments, the sensing electrodes detect one or more other signals received from the target modulation location in addition to, or in lieu of the level of neuronal activation or neuronal firing rates, such as evoked compound action potentials, local field potentials, multiunit activity, electroencephalograms, electrophysiology, or electroneurograms. In at least some embodiments, one or more of the received signals (e.g., evoked compound action potentials, local field potentials, multiunit activity, electroencephalograms, electrophysiology, electroneurograms, or the like) can be used to indirectly measure the level of neuronal activation, or neuronal firing rates, or both, at the target modulation location. In at least some embodiments, the sensing electrodes or other sensors on, or proximate to, the optical modulation lead can detect or measure temperature or heat.

Optionally, the processor 374 can select one or more stimulation electrodes to provide electrical stimulation, if desired. In some embodiments, the processor 374 selects which of the optional stimulation electrode(s) are cathodes and which electrode(s) are anodes.

Any processor can be used and can be as simple as an electronic device that, for example, produces optical modulation at a regular interval or the processor can be capable of receiving and interpreting instructions from an external programming unit 378 that, for example, allows modification of modulation characteristics. In the illustrated embodiment, the processor 374 is coupled to a receiver 372 which, in turn, is coupled to the optional antenna 388. This allows the processor 374 to receive instructions from an external source to, for example, direct the modulation characteristics and the selection of electrodes, if desired.

In one embodiment, the antenna 388 is capable of receiving signals (e.g., RF signals) from an external telemetry unit 376 which is programmed by the programming unit 378. The programming unit 378 can be external to, or part of, the telemetry unit 376. The telemetry unit 376 can be a device that is worn on the skin of the user or can be carried by the user and can have a form similar to a pager, cellular phone, or remote control, if desired. As another alternative, the telemetry unit 376 may not be worn or carried by the user but may only be available at a home station or at a clinician's office. The programming unit 378 can be any unit that can provide information to the telemetry unit 376 for transmission to the optical modulation system 370. The programming unit 378 can be part of the telemetry unit 376 or can provide signals or information to the telemetry unit 376 via a wireless or wired connection. One example of a suitable programming unit is a computer operated by the user or clinician to send signals to the telemetry unit 376.

The signals sent to the processor 374 via the antenna 388 and the receiver 372 can be used to modify or otherwise direct the operation of the optical modulation system. For example, the signals may be used to modify the modulation characteristics of the optical modulation system such as modifying one or more of modulation duration, pulse frequency, waveform, on or off cycling periods, and modulation intensity. The signals may also direct the optical modulation system 370 to cease operation, to start operation, to start charging the battery, or to stop charging the battery. In other embodiments, the optical modulation system does not include the antenna 388 or receiver 372 and the processor 374 operates as programmed.

Optionally, the optical modulation system 370 may include a transmitter (not shown) coupled to the processor 374 and the antenna 388 for transmitting signals back to the telemetry unit 376 or another unit capable of receiving the signals. For example, the optical modulation system 370 may transmit signals indicating whether the optical modulation system 370 is operating properly or not or indicating when the battery needs to be charged or the level of charge remaining in the battery. The processor 374 may also be capable of transmitting information about the modulation characteristics so that a user or clinician can determine or verify the characteristics.

Conventionally, measurements of optical output of an optical lead are made at the light source or at the site(s) of light emission from the lead. Examples of such measurements are presented in U.S. Patent Applications Publication Nos. 2021/0008388; 2021/0008389; and 2021/0016111, all of which are incorporated by reference in their entireties.

In contrast, as described herein, a system can provide to a user an estimated irradiance or modulation dosage at a target based, in part, on device parameters and the distance of the light emitter(s) from the target. In at least some instances, the estimated irradiance can facilitate more accurate dosing than an estimate of output at the light source or the lead because intervening tissue and other factors can reduce the actual amount of light received at the target. Dosages and parameter selection can be dependent on the target. In at least some embodiments, the modulation dosage can be the amount of energy delivered over a specified, preselected, selected, or predetermined period of time.

It will be recognized that there can be multiple targets. In at least some embodiments, the methods and systems described herein can receive multiple targets and provide information, estimates, or the like accounting for the multiple targets. For example, optical modulation may be directed to two targets such as the substantia nigra pars reticulata (SNr) and the nucleus basalis of Meynert.

Figure 4A:
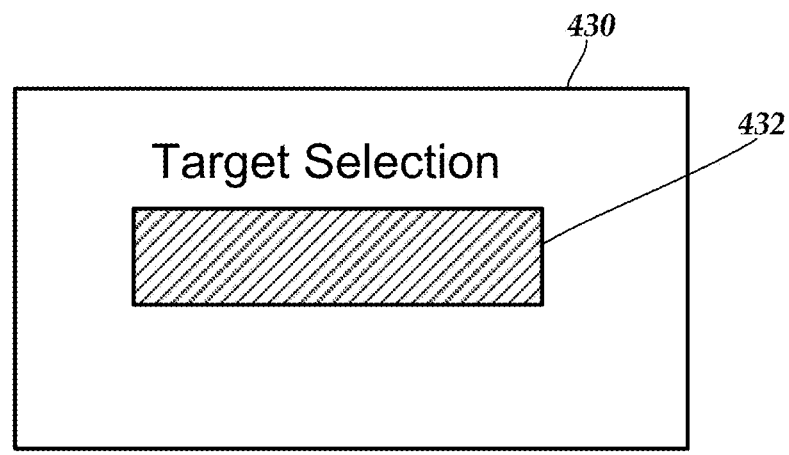
FIG. 4A is a schematic illustration of one embodiment of a user interface for selecting a target.
Figure 4B:
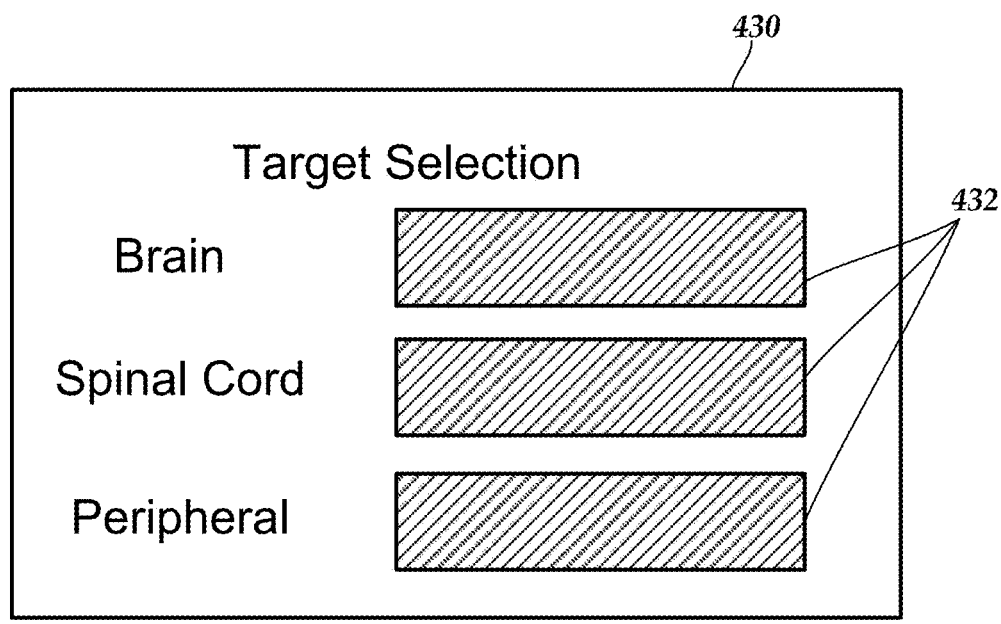
FIG. 4B is a schematic illustration of another embodiment of a user interface for selecting a target.

An optical modulation system or a method for optical modulation can include one or more user interfaces for user selection, modification, or alteration of aspects of the optical modulation. For example, a user interface can be target specific or can allow for receiving one or more targets. The receiving of a target can include, but is not limited, to selecting a target or obtaining a target from a device, software, or any other suitable source. For example, FIG. 4A illustrates one embodiment of a user interface 430 for target selection including a selection control 432 for picking a target. The selection control 432 can be a drop-down menu, any other type of menu, a box for typing in the target, importing data that encodes the target (followed by selecting the target), or any other suitable mechanism for selecting a target. For example, a menu of targets can include a list of anatomical regions, such as regions of the brain. FIG. 4B illustrates another user interface 430 which includes a selection control 432 for each of the different types of modulation including, for example, brain modulation, spinal cord modulation, and peripheral (e.g., peripheral nerve) modulation. For example, the selection control 432, when selected, can present a menu of targets for that type of modulation. As an example, for brain modulation, the targets can be regions of the brain such as, for example, the substantia nigra, nucleus basalis of Meynert, or the like. As another example, for the spinal cord modulation, the targets can be different vertebral locations or vertebral structures, such as the dorsal roots, dorsal columns, dorsal horns, dorsal root ganglia, or the like. For peripheral nerve modulation, a menu of different nerves can be presented. It will be recognized that the features (or select features) of any of the user interfaces described herein can be combined with the features (or select features) of any one or more of the other user interfaces described herein.

Figure 5:
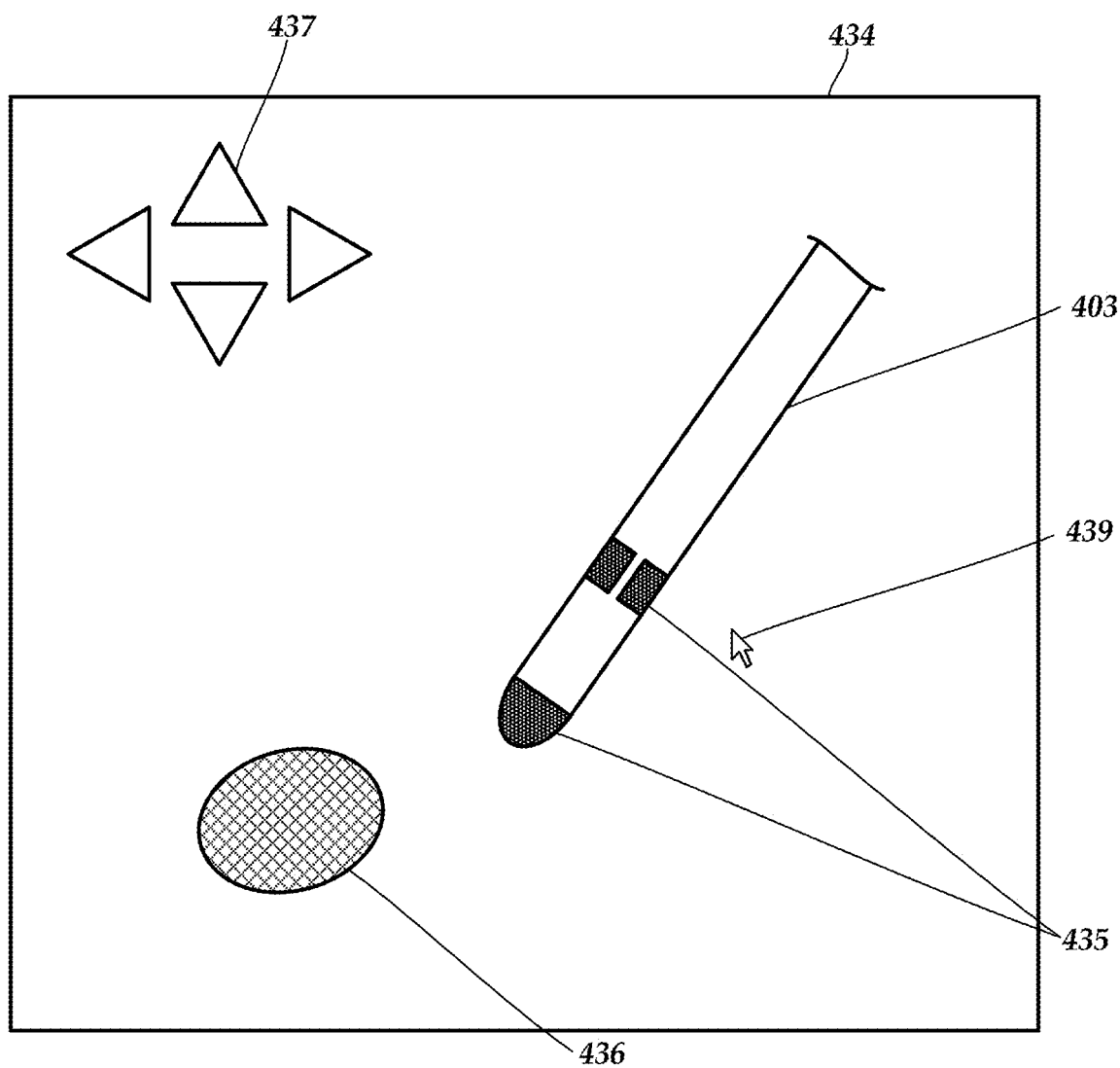
FIG. 5 is a schematic illustration of one embodiment of a user interface for representing the placement of a lead relative to a target.

In at least some embodiments, a user interface 434, such as illustrated in FIG. 5, can include the selected target 436 and allow the user to place a lead 403, with one or more light emitters 435, at a position relative to the target based on the user's knowledge or estimation, imaging, or any other information. In at least some embodiments, the user interface 434 can include movement controls 437 for moving the lead 403 within the user interface. In at least some embodiments, the user interface 434 can include a pointer 439 or other mechanism that can be used to move the lead 403 within the user interface (for example, by a drag-and-drop or point-and-click activity.)

Alternatively or additionally, in at least some embodiments, the lead 403 can be placed by the system. Such placement can be based on information provided to the system from the clinician performing the implantation, from any other individual with knowledge or estimation of the lead implantation site, from surgical planning software, from imaging, or the like or any combination thereof.

In at least some embodiments, the user interface 434 presents the lead 403 and target 436 in a two-dimensional plane or a pseudo-three-dimensional arrangement. In at least some embodiments, the lead 403 and target 436 are presented in a plane (or slice) that intersects both the lead and the target.

It will be understood that the light emitter 435 can be a light source or can be an emission region of an optical fiber, fiber optic, or optical waveguide that is coupled to a light source. In at least some embodiments, multiple light sources can be used. In at least some embodiments, a lead can have multiple light sources or light emission regions.

In at least some embodiments, multiple light sources can be used. The multiple light sources can emit light having the same wavelength or wavelength range or two or more of the light sources can differ in wavelength or wavelength range. In at least some embodiments with light sources that differ in wavelength or wavelength range, the user can select the wavelength or wavelength range for the illumination.

In at least some embodiments, there can be two or more leads 403—at least one lead for each hemisphere of the brain or different leads for different medial-lateral or rostral-caudal locations along the spine or different leads for different nerve branches. In at least some embodiments, the user interface 434 (or any other user interface described herein) can show both leads 403 (either in one display area or two display areas) or can be toggled between the two leads.

In at least some embodiments, a user, such as a physician or clinician, can estimate the distance from the light emitter(s) on the lead 403 to the target. In at least some embodiments, information about the target (for example, type, location, branch, or the like) can be used to estimate the distance from the light emitter(s) on the lead to the target. Other information can be used by the system to estimate the distance information provided to the system from a variety of sources including, but not limited to, the clinician performing the implantation, any other individual with knowledge, or estimation, of the lead implantation site, surgical planning software, imaging, or the like or any combination thereof.

In at least some embodiments, anatomical information, imaging, or other information can be used to identify or estimate the tissue (and corresponding tissue properties) that is between the light emitter and the target. In at least some embodiments, the system can utilize a model, equation, or other arrangement for estimating the light distribution within the tissue. Such model, equation, or other arrangement can account for factors such as, for example, the target itself and light attenuation arising from the tissue between the light emitter(s) and the target. Such models can estimate light attenuation arising from one or more of the following: light absorption, scattering, reflection, refraction, or the like or any combination thereof.

In at least some embodiments, an estimated light distribution can be determined using simulations. In at least some embodiments, an estimated light distribution can be determined from a look-up table, an analytical estimation, or other arrangement that is based on modulations conducted previously. In at least some embodiments, an estimated light distribution may be enhanced or updated based on simulations that occur in the background or offline.

Figure 6A:
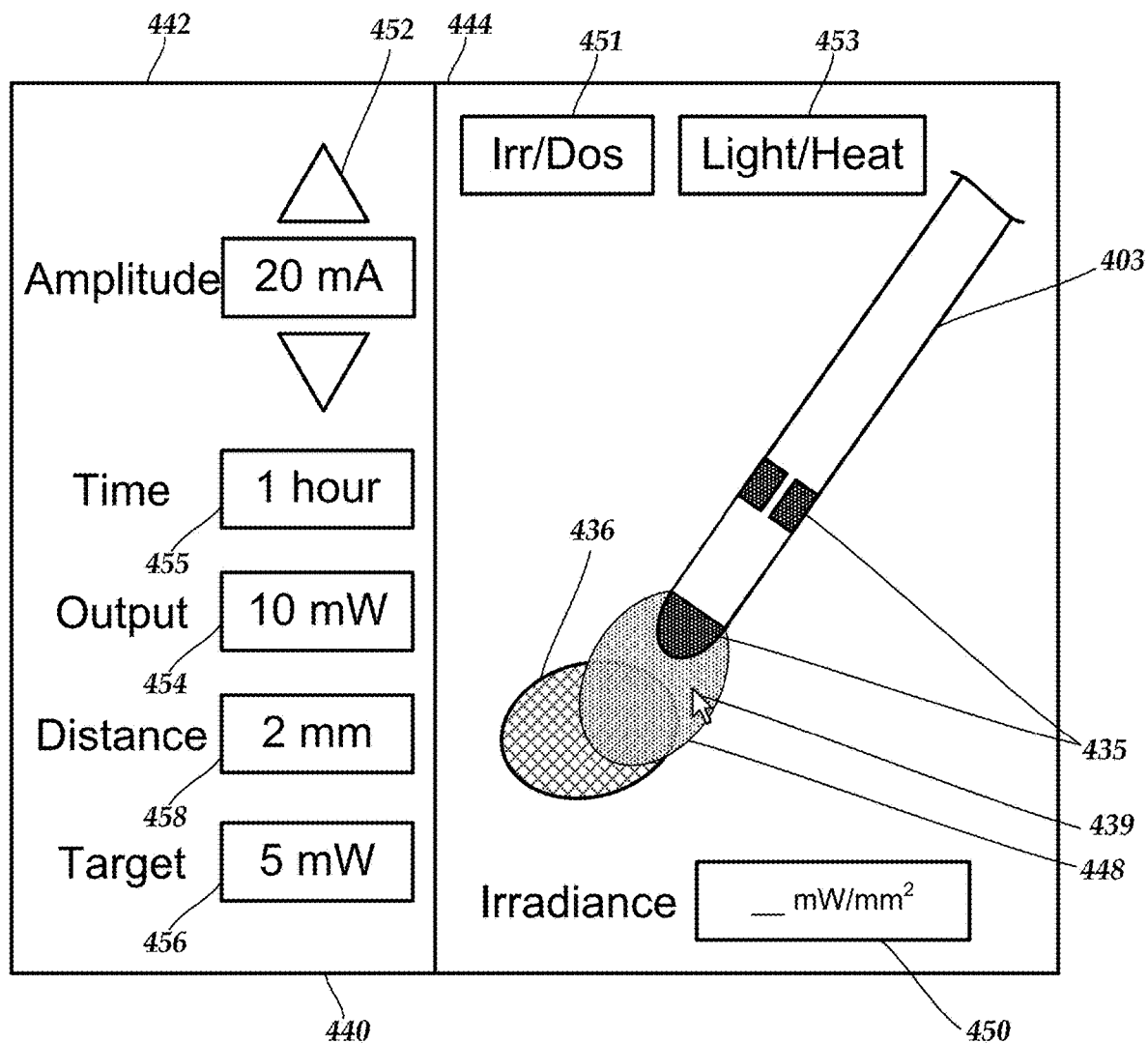
FIG. 6A is a schematic illustration of one embodiment of a user interface for controlling and estimating an effect of optical modulation.

FIG. 6A illustrates one embodiment of a user interface 440 that includes a dose control section 442 and an optional display section 444. In at least some embodiments, the display section 444 includes a representation of the lead 403 and the target 436. The representation of the lead 403 can also include the representation of one or more light emitters 435. In at least some embodiments, the display section 444 can include a pointer 439 that can be moved over the display section by the user.

In at least some embodiments, the display section 444 can include a representation of a light distribution 448 generated by the light emitter(s) 435 according to the current optical modulation parameters. In at least some embodiments, the representation of the light distribution 448 may be limited to, or bounded by, only that area that receives a predetermined or user-selected threshold value of irradiance or modulation dosage. In at least some embodiments, the user can modify the minimum value. In at least some embodiments, the light distribution 448 can be displayed as a pseudo-color, gray-scale, or contour plot. In at least some embodiments, the representation of the estimated light distribution using colors, shades, or contour line(s) to delineate regions based on an estimated amount of irradiance or modulation dosage received in each of the regions. In at least some embodiments, such plots may select color, gray-scale, or contour line(s) that are normalized based on irradiance power. In at least some embodiments, the light distribution is illustrated using a single contour line or a volume that corresponds to irradiance or modulation dosage at or above a threshold amount. In at least some embodiments, a user can set or modify the threshold amount used to determine the single contour line or volume.

In at least some embodiments, the display section 444 may also include a value 450 of the estimated irradiance or modulation dosage at the target 436. This value 450 may be an average value for the target 436, a value at the nearest point of the target to the light emitter(s) 435, a value at a center of the target, or any other suitable value that represents irradiance or modulation dosage at the target. In at least some embodiments, the display section 444 can include any one or more of the following statistical values of irradiance or modulation dosage of the target, such as, for example, a mean, range, or standard deviation. In at least some embodiments, the value 450 of estimated irradiance or modulation dosage may also depend on light source performance over time and determinations of such values may be adjusted during the lifetime of the light source.

In at least some embodiments, the value 450 (or another value display) represents the estimated irradiance or modulation dosage at the point identified by the pointer 439. In at least some embodiments, the system can estimate the value 450 of the irradiance or modulation dosage at the target 436 based on the spot size of the light emitter 435. For example, a spot size estimated to be 1.3 mm may have an irradiance at a target, absent effects arising from intervening tissue, of 4.77 mW/mm$^2$.

In at least some embodiments, the user interface 440 can include a control 451 to select or switch between different views of the representation of light distribution 439, value 450, or both. For example, the control 451 be used to can select or switch between the value 450 being irradiance or modulation dosage. As another example, the control 451 can be used to select between a representation of a light distribution 439 (or a value 450 for the modulation dosage) that represents an instantaneous light distribution (e.g., irradiance), a light distribution for a bolus (e.g., a portion of the dosage that constitutes a bolus), a light distribution for the entire modulation dosage (e.g., a daily, weekly, or monthly modulation dosage or other modulation dosage over a defined time period), a light distribution over a defined time period (e.g., a minute, hour, day, week, month, or any other defined period of time), or a cumulative light distribution (where, in at least some embodiments, the start time can be defined by the user or system).

Figure 6B:
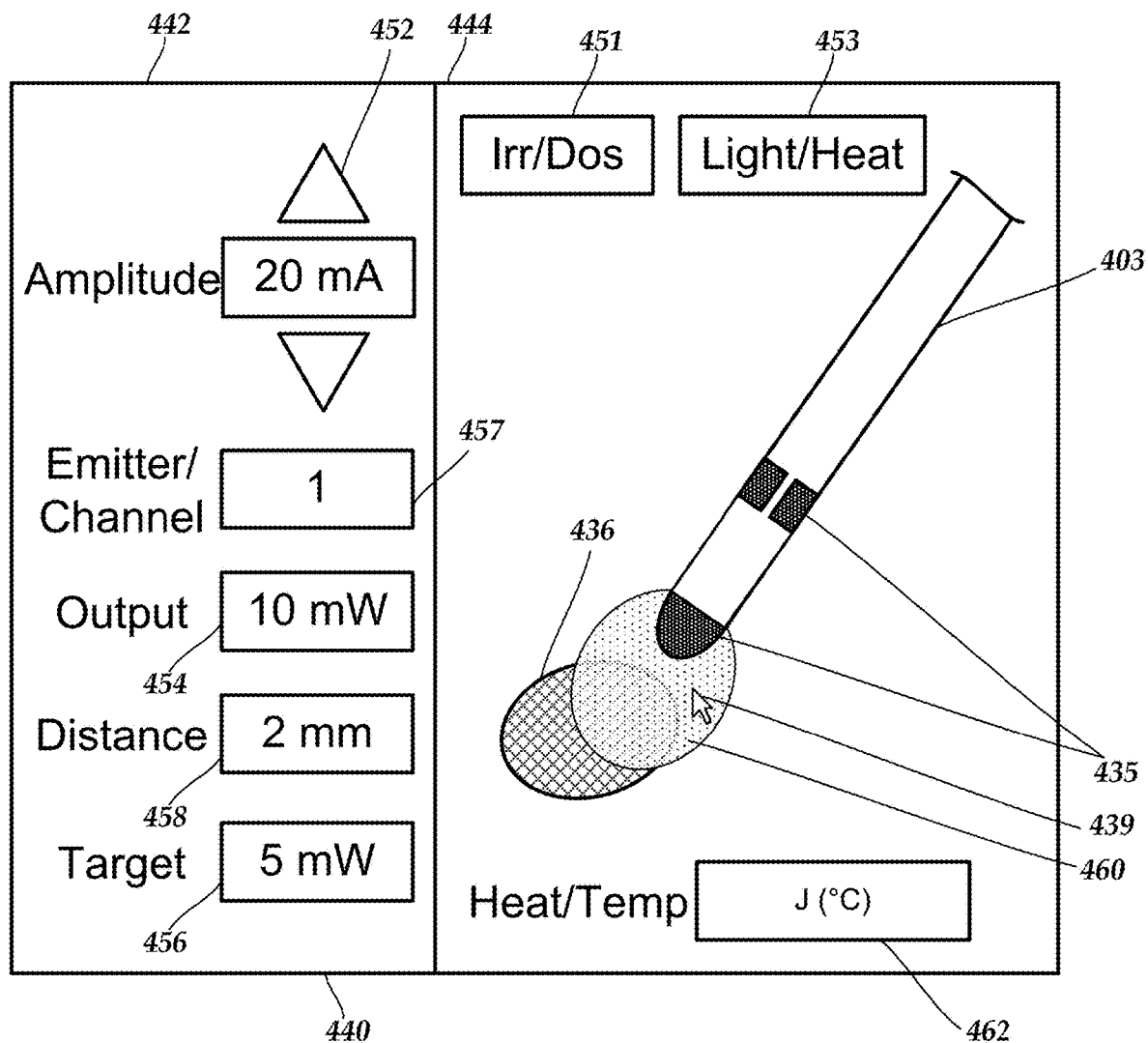
FIG. 6B is a schematic illustration of another embodiment of a user interface for controlling and estimating an effect of optical modulation.

In at least some embodiments, the display section 444 can display estimated heat generation 460 or an estimated temperature or temperature increase in tissue due to the illumination, as illustrated in FIG. 6B. The estimated heat generation, temperature, or temperature increase can be determined and displayed for the target, for intervening or other non-target tissue, or for any combination thereof. Alternatively or additionally, in at least some embodiments, the display section 444 can display estimated heat generation 460 or an estimated temperature or temperature increase in tissue due to the illumination as an overlay around the lead, as a secondary display (for example, as a picture-in-picture arrangement), or using any other suitable display arrangement. In at least some embodiments, the user interface 440 can include a toggle control 453 to toggle between displaying the light distribution 448 or displaying the heat generation 460, temperature, or temperature increase. In at least some embodiments, the estimated heat generation, temperature, or temperature increase is modified based on estimated perfusion or flow of blood which can transport heat away from the site of the estimate.

In at least some embodiments, the display section 444 may also include a value 462 of the estimated heat generation, temperature, or temperature increase at the target 436. This value 462 may be an average value for the target 436, a value at the nearest point of the target to the light emitter(s) 435, a value at a center of the target, or any other suitable value that represents estimated heat generation, temperature, or temperature increase (or any combination thereof) at the target, light emitter, or intervening tissue (or any combination thereof). In at least some embodiments, the display section 444 can include any one or more of the following statistical values of heat generation, temperature, or temperature increase of the target, such as, for example, a mean, range, or standard deviation. In at least some embodiments, the value 462 (or another value display) represents the estimated heat generation, temperature, or temperature increase at the point identified by the pointer 439. In at least some embodiments, a thermal model of the tissue can be used to for estimating heat generation, temperature, or temperature increase.

In FIGS. 6A and 6B, the dose control section 442 can include controls 452 to set or modify parameters such as, for example, amplitude (e.g., amplitude of the current or voltage applied to the light source), modulation intensity, pulse width, pulse rate, burst rate, burst duration, duty cycle, duration of irradiation, wavelength or wavelength range, or the like or any combination thereof. (For ease of illustration, only the control 452 for setting or modifying amplitude is shown.) In at least some embodiments, instead of, or in addition to, setting or modifying an amplitude of the current or voltage applied to the light source, the interface 440 can include controls so that the user can set or modify an output power or output irradiance at the light emitter(s) (control 435) or a desired estimated power or irradiation at the target (control 436). The user interface 440 may also include other information such as the distance 458 between the lead 403 or light emitter(s) 435 and the target 436.

In at least some embodiments, the system may have a preprogrammed default value for one or more of the parameters. In at least some embodiments, the preprogrammed default value(s) may be dependent on the target selected by the user, the type of lead or control module used, or any other suitable conditions or any combination thereof.

In at least some embodiments, the controls 451, 452, 453, 454, 456, 458 can be locked or unlocked by the user, the system, or both. In at least some embodiments, one or more of the parameters can have a preprogrammed upper limit, lower limit, or range. For example, the amplitude or modulation intensity may have an upper limit that can account for one or more of the following: device capabilities, safety, heat generation (with possible damage to tissue or the lead), or the like or any combination thereof.

In at least some embodiments, the selection of a value for at least one of the modulation parameters can be limited by an estimation of a modulation dosage, temperature change, temperature, heating, or delivered energy at the target. This estimation can be based on any number of parameters including, but not limited to, one or more of the target, the location of the optical modulation lead, or the selected value of at least one other of the modulation parameters. In at least some embodiments, the estimation can be defined for a particular period of time (for example, 1, 5, 10, 15, 30, or 90 minutes or 1, 2, 4, 6, or 12 hours, or 1, 2, 5, or 7 days, or the like or any other suitable time period).

In at least some embodiments, the selection of a value for at least one of the modulation parameters can be limited by an estimation of a dosage, temperature change, temperature, heating, or delivered energy at non-target tissue (for example, intervening tissue between the lead 403 and the target 436). This estimation can be based on any number of parameters including, but not limited to, one or more of a location of the non-target tissue, a threshold value, the location of the optical modulation lead, and the selected value of at least one other of the modulation parameters. In at least some embodiments, the estimation can be defined for a particular period of time (for example, 1, 5, 10, 15, 30, or 90 minutes or 1, 2, 4, 6, or 12 hours, or 1, 2, 5, or 7 days, or the like or any other suitable time period).

Examples of systems and methods for estimating dosage, temperature change, temperature, heating, or delivered energy at non-target tissue at target or non-target tissue can be found in U.S. Provisional Patent Application Ser. No. 63/399,982, incorporated herein by reference in its entirety.

In at least some embodiments, the system can include a dosage control (for example, control 456) that limits the delivery of a dosage to a threshold amount. In at least some embodiments, the threshold amount can be user selected or user modified from a default or other value. The threshold amount can correspond to, for example, a level of power delivery, a level of energy delivery, an amount of heat generation at the target or in non-target tissue (for example, intervening tissue), an amount of temperature increase at the target or in non-target tissue, or the like or any combination thereof. In at least some embodiments, the threshold amount can be defined for a particular period of time (for example, 1, 5, 10, 15, 30, or 90 minutes or 1, 2, 4, 6, or 12 hours, or 1, 2, 5, or 7 days, or the like or any other suitable time period). In at least some embodiments, the same controls and considerations can be applied to a bolus of modulation (for example, when the modulation dosage is delivered in two or more boluses) or to continuous modulation.

In at least some embodiments, when the programmed set of parameters is estimated to provide a modulation dosage that exceeds the threshold amount (or generate heat, a temperature, or temperature change above a threshold amount), execution of the set of parameters may be disabled, a warning may be provided to the user, the user interface 440 may display colors or other symbols to indicate that the parameters may be approach or exceed the threshold, or any combination of these actions. For example, parameters may be provided in green, with a green background, or with a green symbol when the generation of light using the parameters will not exceed the threshold amount. Orange can be used when the generation of light using the parameters will likely approach or exceed the threshold amount. Red can be used when the generation of light using the parameters will definitely approach or exceed the threshold amount.

In at least some embodiments, the dose control section 442 also includes an estimated output section which can include information such as the light output 454 (e.g., output power or output irradiance) at the light emitter(s), the distance 448 to the target, and the estimated irradiance or power 456 at the target. The light output 454 is related to parameters such as, amplitude or intensity of light emission (for example, measured in mW), amplitude of the current or voltage that drives the light source, pulse width, and pulse rate. In at least some embodiments, the system estimates the light output 454 based on one or more of these parameters, as explained above.

In the case the that the light emitter(s) 435 is/are not a light source, the system or user may account for losses between the light source(s) and the light emitter(s) when selecting the output power or output irradiance. In at least some embodiments, the output power or output irradiance can be estimated using a transfer function, a calibration table, a calibration formula, or from previous measurement (s). In at least some embodiments, the lead or light source can have an associated light monitor that measures the output power or output irradiance at the light emitter(s) 435 or at the light source. In at least some embodiments, the output power or output irradiance can be expressed as peak irradiant power (mW) or average irradiant power (mW) or any combination thereof. Additional dose information can include the energy per pulse (Joules/pulse).

In at least some embodiments, the power or irradiance at the target can be estimated using a transfer function or from previous measurement(s). In at least some embodiments, power or irradiance at the target can be expressed as peak irradiant power (mW) or average irradiant power (mW) or any combination thereof.

In at least some embodiments, time parameters are reflected in the estimated output power or output irradiance or the estimates are estimates of the energy delivered over a certain period of time. In at least some embodiments, the unit of time is a day, an hour, a minute, or a second, or any other suitable period of time or the unit of time can be a dose (e.g., the amount of irradiance or modulation dosage provided in a day or other suitable time period) or a bolus (e.g., the amount of irradiance or modulation dosage provided as a particular portion of a dose). Time parameters can include, for example, pulse width, pulse rate, duty cycle, selection as continuous wave illumination, duration of a dose or bolus, the number of doses or boluses per day, week, month, or other suitable time period. In at least some embodiments, when a time parameter is set or modified using, for example, a time control 455 (FIG. 6A), the user interface 440 alters the estimated output power, output irradiance, or energy delivered over a certain period of time.

In at least some embodiments, a user can select an energy or modulation dosage (for example, an output 454 at the light emitter or an output 456 at the target) to be delivered (for example, to be delivered per unit of time or to be delivered as a modulation dosage). In at least some embodiments, the system can automatically recommend other parameters, such as amplitude, light emitter selection, pulse width, pulse duration, or the like or any combination thereof, to provide the desired energy.

In at least some embodiments, the user interface 440 can permit the programming of multiple light emitters 435 which can be used simultaneously, sequentially, or in any other arrangement. The dose control section 442 can include a control 457 (FIG. 6B) to select the light emitter(s) for which the current parameters are displayed or available to set or modify.

In at least some embodiments, the user interface 440 can permit the programming of multiple channels (one or more optical modulation channels, one or more electrical stimulation channels, or any combination thereof) or multiple programs (one or more optical modulation programs, one or more electrical stimulation programs, or any combination thereof) which can be used simultaneously, sequentially, or in any other arrangement. In at least some embodiments, controls for optical modulation channels or programs may differ from controls for electrical stimulation channels or programs. The dose control section 442 can include a control 457 (FIG. 6B) to select the channel for which the current parameters are displayed or available to set or modify.

The systems and methods can be used for optogenetic illumination as well. Perfusion of a viral vector or other genetic-modifying agent or photosensitizing agent can facilitate optogenetics therapy or photodynamic therapy. In at least some embodiments, the display section 444 can also display an estimate of perfusion of a viral vector or other genetic-modifying agent or photosensitizing agent. In at least some embodiments, the system can utilize the selected parameters (for example, wavelength selection, illumination parameter selection, and the target selection) to estimate an optogenetic or photodynamic effect.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (e.g., RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

It will be understood that each of the methods disclosed herein, can be implemented by computer program instructions. These program instructions may be provided to a processor to produce a machine, such that the instructions, which execute on the processor, create means for implementing the actions. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An optical modulation system, comprising:
a display;
a memory comprising instructions;
a processor coupled to the display and the memory and configured to execute the instructions, wherein the instructions comprise
presenting, on the display, a user interface comprising a plurality of user-selectable controls to select or adjust values for each of a plurality of modulation parameters;
receiving a target;
receiving or determining a location of an optical modulation lead relative to the target;
receiving a selection of the value for each of the modulation parameters;
presenting, on the display, a representation of the optical modulation lead and a representation of the target relative to the location of the optical modulation lead;
estimating a modulation dosage or irradiance at the target based on, at least, the target, the location of the optical modulation lead, the values of the modulation parameters, and estimated light attenuation by tissue between the optical modulation lead and the target; and
presenting, on the display, a value of the estimated modulation dosage or irradiance at the target.

2. The optical modulation system of claim 1, wherein the instructions further comprise presenting, on the display, a pointer and the value of the estimated modulation dosage or irradiance at a site of the pointer relative to the representation of the optical modulation lead.

3. The optical modulation system of claim 1, wherein the value of the estimated modulation dosage or irradiance at the target is an instantaneous value of the estimated irradiance at the target.

4. The optical modulation system of claim 1, wherein the value of the estimated modulation dosage or irradiance at the target is a cumulative value of the estimated modulation dosage delivered at the target for a selected period of time.

5. The optical modulation system of claim 1, wherein the value of the estimated modulation dosage or irradiance at the target is a value of the estimated modulation dosage delivered at the target for a predefined modulation dosage period.

6. The optical modulation system of claim 1, wherein the instructions further comprise presenting, on the display, a representation of an estimated light distribution.

7. The optical modulation system of claim 6, wherein presenting the representation of the estimated light distribution comprises presenting the representation of the estimated light distribution using a plurality of colors, a plurality of shades, or at least one contour line to delineate regions based on a) an estimated amount of irradiance or modulation dosage received in each of the regions or b) an estimated temperature or temperature change for each of the regions.

8. An optical modulation system, comprising:
a display;
a memory comprising instructions;
a processor coupled to the display and the memory and configured to execute the instructions, wherein the instructions comprise
presenting, on the display, a user interface comprising a plurality of user-selectable controls to select or adjust values for each of a plurality of modulation parameters;
receiving a target;
receiving or determining a location of an optical modulation lead relative to the target;
receiving a selection of the value for each of a plurality of the modulation parameters;
estimating a modulation dosage at the target based on, at least, the target, the location of the optical modulation lead, and the selected values of the modulation parameters, and at least one of a) estimated light attenuation by tissue between the optical modulation lead and the target or b) estimated light distribution with the tissue; and
presenting, on the display, a value of the estimated modulation dosage at the target.

9. The optical modulation system of claim 8, wherein the instructions further comprise presenting, on the display, a representation of the optical modulation lead and a representation of the target relative to the location of the optical modulation lead.

10. The optical modulation system of claim 8, wherein the instructions further comprise presenting, on the display, a representation of an estimated light distribution.

11. The optical modulation system of claim 10, wherein presenting the representation of the estimated light distribution comprises presenting the representation of the estimated light distribution using a plurality of colors, a plurality of shades, or at least one contour line to delineate regions based on a) an estimated amount of irradiance or modulation dosage received in each of the regions or b) an estimated temperature or temperature change for each of the regions.

12. An optical modulation system, comprising:
a display;
a memory comprising instructions;
a processor coupled to the display and the memory and configured to execute the instructions, wherein the instructions comprise
presenting, on the display, a user interface comprising a plurality of user-selectable controls to select or adjust values for each of a plurality of modulation parameters;
receiving a target;
receiving or determining a location of an optical modulation lead relative to the target;
estimating and presenting, on the display, either a) a modulation dosage, temperature change, temperature, heating, or delivered energy at the target based on, at least, the target, the location of the optical modulation lead, and the selected value of at least one other of the modulation parameters or b) a dosage, temperature change, temperature, heating, or delivered energy at non-target tissue based on, at least, a location of the non-target tissue, a threshold value, the location of the optical modulation lead, and the selected value of at least one other of the modulation parameters; and
receiving a selection of the value for each of a plurality of the modulation parameters, wherein the selection of the value of at least one of the modulation parameters is limited by at least one of a) the estimation of the modulation dosage, temperature change, temperature, heating, or delivered energy at the target based on, at least, the target, the location of the optical modulation lead, and the selected value of the at least one other of the modulation parameters or b) the estimation of the dosage, temperature change, temperature, heating, or delivered energy at non-target tissue based on, at least, the location of the non-target tissue, the threshold value, the location of the optical modulation lead, and the selected value of the at least one other of the modulation parameters.

13. The optical modulation system of claim 12, wherein the value of the at least one of the modulation parameters that is limited is a value of a modulation intensity.

14. The optical modulation system of claim 12, wherein the estimation of the modulation dosage is an estimation of the modulation dosage over a predefined modulation dosage period.

15. The optical modulation system of claim 12, wherein the estimation of the modulation dosage, temperature change, temperature, heating, or delivered energy at the non-target tissue is an estimation of the modulation dosage, temperature change, temperature, heating, or delivered energy at the non-target tissue over a predefined period of time.

16. The optical modulation system of claim 12, wherein the value of the at least one of the modulation parameters is limited when the estimation of the modulation dosage or the estimation of the modulation dosage, temperature change, temperature, heating, or delivered energy at the non-target tissue exceeds a preselected value.

17. The optical modulation system of claim 12, wherein the instructions further comprise presenting, on the display, a representation of an estimated light distribution.

18. The optical modulation system of claim 17, wherein presenting the representation of the estimated light distribution comprises presenting the representation of the estimated light distribution using a plurality of colors, a plurality of shades, or at least one contour line to delineate regions based on an estimated amount of irradiance or modulation dosage received in each of the regions.

19. The optical modulation system of claim 17, wherein presenting the representation of the estimated light distribution comprises presenting the representation of the estimated light distribution using a plurality of colors, a plurality of shades, or at least one contour line to delineate regions based on an estimated temperature or temperature change for each of the regions.

\* \* \* \* \*